United States Patent
Akita et al.

(10) Patent No.: US 12,053,568 B2
(45) Date of Patent: Aug. 6, 2024

(54) BLOOD PURIFICATION APPARATUS

(71) Applicant: Nikkiso Company Limited, Tokyo (JP)

(72) Inventors: Kunihiko Akita, Shizuoka (JP); Shinya Hasegawa, Shizuoka (JP); Masahiro Toyoda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 802 days.

(21) Appl. No.: 17/072,270

(22) Filed: Oct. 16, 2020

(65) Prior Publication Data

US 2021/0052799 A1  Feb. 25, 2021

Related U.S. Application Data

(63) Continuation of application No. PCT/JP2019/016899, filed on Apr. 19, 2019.

(30) Foreign Application Priority Data

Apr. 26, 2018 (JP) ................................ 2018-085075

(51) Int. Cl.
*A61M 1/36* (2006.01)
*A61M 1/34* (2006.01)
*A61M 60/113* (2021.01)

(52) U.S. Cl.
CPC ............ *A61M 1/3601* (2014.02); *A61M 1/34* (2013.01); *A61M 1/3659* (2014.02);
(Continued)

(58) Field of Classification Search
CPC .... A61M 1/3601; A61M 1/34; A61M 1/3659; A61M 60/113; A61M 1/3626;
(Continued)

(56) References Cited

U.S. PATENT DOCUMENTS 3,441,136 A    4/1969  Wilson
4,231,366 A *  11/1980  Schael .................. A61M 1/303
                                                 604/6.11
(Continued)

FOREIGN PATENT DOCUMENTS

CN    101920049 A    12/2010
EP       2005982 A1    12/2008
(Continued)

OTHER PUBLICATIONS

European Search Report for corresponding Application No. 19792790.8, dated Oct. 20, 2021.
(Continued)

*Primary Examiner* — Leslie A Lopez
*Assistant Examiner* — Quynh Dao Le
(74) *Attorney, Agent, or Firm* — Young Basile Hanlon & MacFarlane, P.C.

(57) ABSTRACT

A blood purification apparatus that includes a blood circuit including an arterial blood circuit provided with an arterial puncture needle and a venous blood circuit provided with a venous puncture needle with which an access vessel is puncturable, the blood circuit allowing blood of the patient to extracorporeally circulate; a blood purifier connected to the arterial blood circuit and to the venous blood circuit and that purifies the blood flowing through the blood circuit; a blood pump provided to the arterial blood circuit; a recirculating-blood-detecting unit capable of detecting recirculating blood when the blood of the patient is caused to extracorporeally circulate through the blood circuit by activating the blood pump, the recirculating blood being blood once returned to the patient from the venous blood circuit and reintroduced into the arterial blood circuit; and a recirculation-rate-calculating unit capable of calculating recircu-
(Continued)

lation rate, the recirculation rate being a proportion of the recirculating blood in the blood flowing in the arterial blood circuit. The blood purification apparatus includes a control unit capable of executing a treatment mode in which blood purification treatment is performed with the blood purifier while the blood of the patient is caused to extracorporeally circulate through the blood circuit by activating the blood pump in a state of normal connection where an upstream part of the access vessel is punctured with the puncture needle at a distal end of the arterial blood circuit and a downstream part of the access vessel is punctured with the puncture needle at a distal end of the venous blood circuit; and a measurement mode in which the detection of recirculating blood by the recirculating-blood-detecting unit and the calculation of recirculation rate by the recirculation-rate-calculating unit are performed while the blood of the patient is caused to extracorporeally circulate through the blood circuit by activating the blood pump in a state of reverse connection where the downstream part of the access vessel is punctured with the puncture needle at the distal end of the arterial blood circuit and the upstream part of the access vessel is punctured with the puncture needle at the distal end of the venous blood circuit, the calculated recirculation rate being used in calculating blood flow rate in the access vessel that is calculable in the measurement mode.

20 Claims, 5 Drawing Sheets

(52) U.S. Cl.
CPC ......... *A61M 60/113* (2021.01); *A61M 1/3626* (2013.01); *A61M 1/3661* (2014.02); *A61M 2205/3331* (2013.01)

(58) Field of Classification Search
CPC .............. A61M 1/3661; A61M 1/3658; A61M 1/3609; A61M 1/3621; A61M 1/3653; A61M 1/3655; A61M 2205/3331; A61M 2205/3306; A61M 2205/3334; A61M 2205/3379; A61M 2205/3393; A61M 2205/3396; A61M 2205/3337; A61M 25/0026; A61M 5/1582; A61M 60/37; A61B 5/026

See application file for complete search history.

(56) References Cited

U.S. PATENT DOCUMENTS

| | | | | |
|---|---|---|---|---|
| 5,830,365 | A * | 11/1998 | Schneditz | A61M 1/3427 604/6.11 |
| 6,117,099 | A * | 9/2000 | Steuer | A61M 1/3655 604/4.01 |
| 6,153,109 | A * | 11/2000 | Krivitski | A61M 1/3653 210/85 |
| 6,187,199 | B1 | 2/2001 | Goldau | |
| 6,666,840 | B1 | 12/2003 | Falkvall et al. | |
| 7,147,616 | B2 | 12/2006 | Pedrazzi et al. | |
| 7,488,301 | B2 | 2/2009 | Beden et al. | |
| 7,959,593 | B2 | 6/2011 | Ueda et al. | |
| 8,991,414 | B2 | 3/2015 | Gronau et al. | |
| 2004/0129616 | A1 * | 7/2004 | Mori | A61M 1/1613 210/85 |
| 2004/0204634 | A1 | 10/2004 | Womble et al. | |
| 2006/0254982 | A1 * | 11/2006 | Kopperschmidt | A61M 1/3434 210/90 |
| 2008/0076182 | A1 | 3/2008 | Takahashi et al. | |
| 2008/0103427 | A1 | 5/2008 | Toyoda et al. | |
| 2009/0088683 | A1 | 4/2009 | Roger et al. | |
| 2010/0084326 | A1 * | 4/2010 | Takesawa | A61M 1/36226 264/296 |
| 2010/0274172 | A1 | 10/2010 | Guenther et al. | |
| 2011/0144459 | A1 | 6/2011 | Akita et al. | |
| 2012/0228226 | A1 | 9/2012 | Castellarnau et al. | |
| 2013/0012861 | A1 * | 1/2013 | Zhang | A61M 1/3656 604/6.16 |
| 2013/0150766 | A1 * | 6/2013 | Olde | A61M 1/3661 604/4.01 |
| 2014/0291244 | A1 | 10/2014 | Wolff | |
| 2016/0045657 | A1 * | 2/2016 | Krause | A61M 1/3656 210/96.2 |
| 2017/0157310 | A1 * | 6/2017 | Scarpaci | A61M 1/288 |
| 2019/0134290 | A1 * | 5/2019 | Pouchoulin | A61M 1/1609 |
| 2020/0038572 | A1 * | 2/2020 | Sternby | A61M 1/1615 |
| 2020/0188572 | A1 * | 6/2020 | Maierhofer | A61M 1/3672 |

FOREIGN PATENT DOCUMENTS

| | | |
|---|---|---|
| EP | 2292284 A1 | 3/2011 |
| JP | S60-153138 U | 10/1985 |
| JP | H06-047090 B2 | 6/1994 |
| JP | 2003-519539 A | 6/2003 |
| JP | 2004-016619 A | 1/2004 |
| JP | 2006-280775 A | 10/2006 |
| JP | 2007-007435 A | 1/2007 |
| JP | 2007-020962 A | 2/2007 |
| JP | 2007-135885 A | 6/2007 |
| JP | 2007-167108 A | 7/2007 |
| JP | 2009-112651 A | 5/2009 |
| JP | 2009-131412 A | 6/2009 |
| JP | 2010-136841 A | 6/2010 |
| JP | 2010-184029 A | 8/2010 |
| JP | 2010-269050 A | 12/2010 |
| JP | 2010-273784 A | 12/2010 |
| JP | 2011-120821 A | 6/2011 |
| JP | 2011-120822 A | 6/2011 |
| JP | 2011-120823 A | 6/2011 |
| JP | 2017-012648 A | 1/2017 |
| WO | 96/08305 A1 | 3/1996 |
| WO | 98/17193 A1 | 4/1998 |
| WO | 99/62574 A1 | 12/1999 |
| WO | 2001/051106 A1 | 7/2001 |
| WO | WO-2017006947 A1 * | 1/2017 ............ A61B 5/026 |
| WO | 2017/140424 A2 | 8/2017 |
| WO | 2017165933 A1 | 10/2017 |

OTHER PUBLICATIONS

Techwalla, What is the Difference Between a Microcomputer & a Minicomputer?, Apr. 7, 2011, p. 1.

* cited by examiner

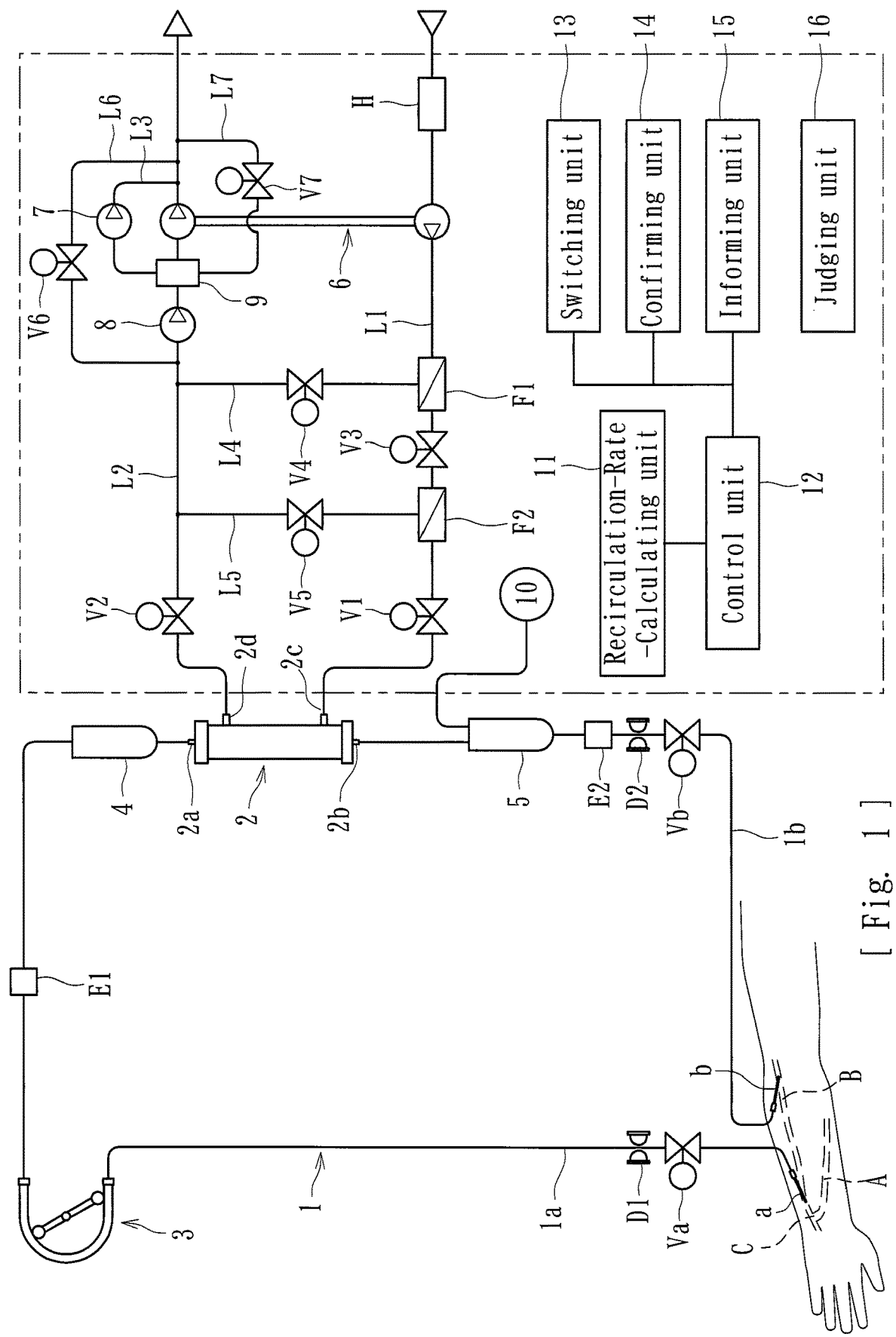
[Fig. 1]

[Fig. 2]
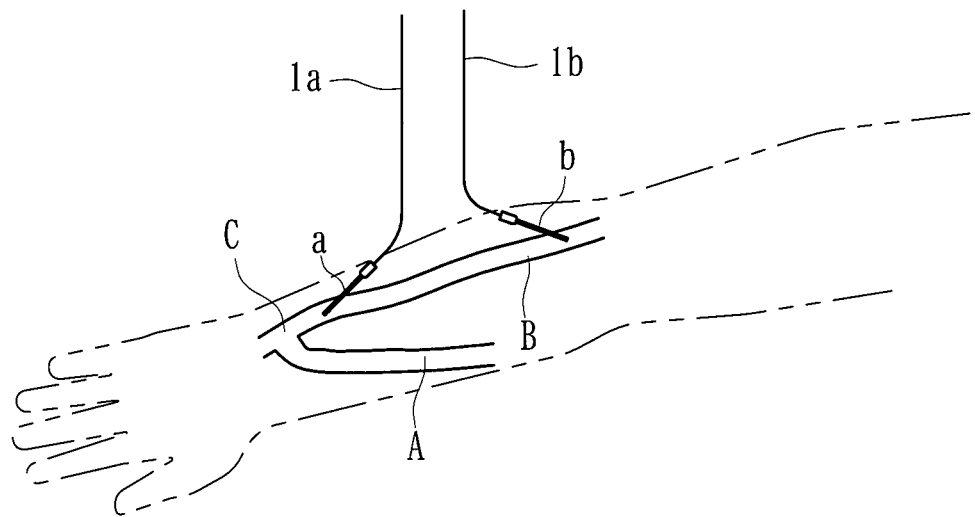
[Fig. 3]
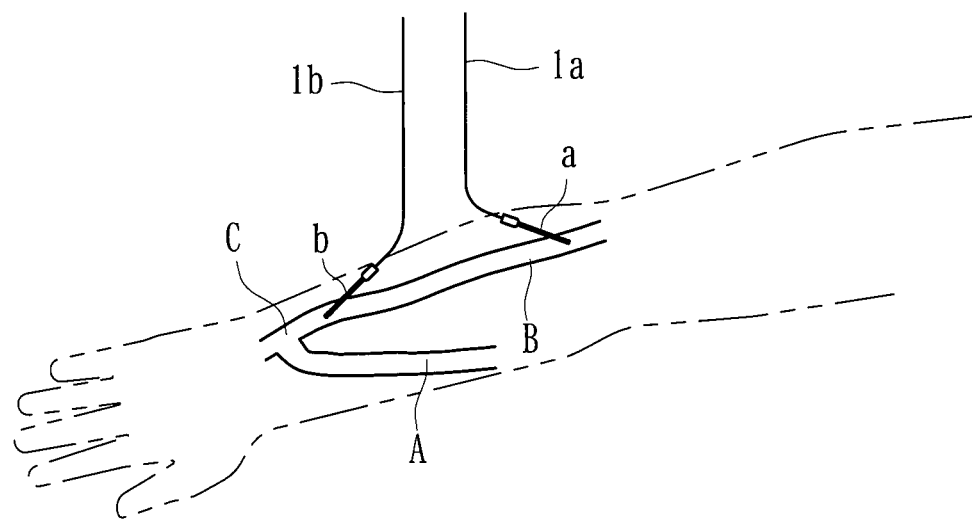

[Fig. 4]
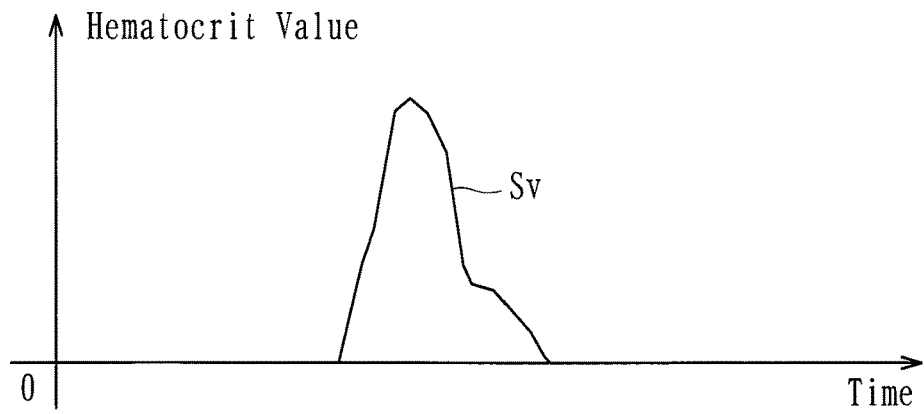
[Fig. 5]
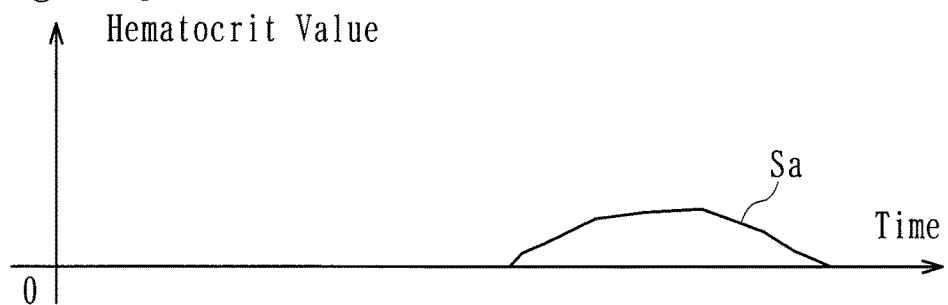
[Fig. 6]
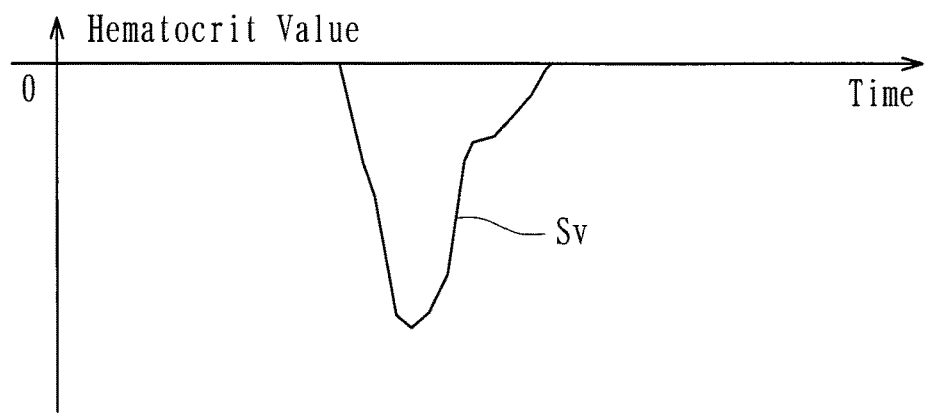
[Fig. 7]
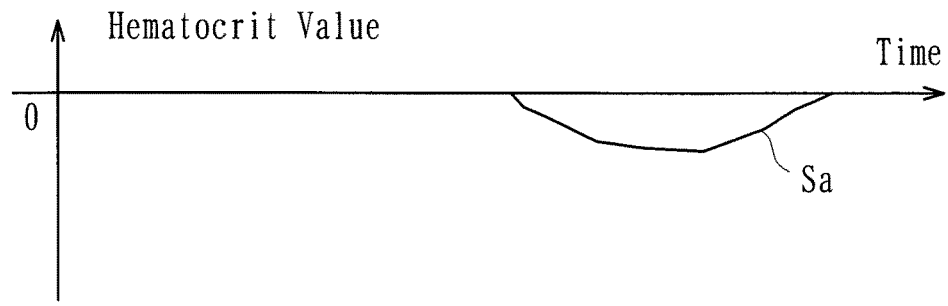

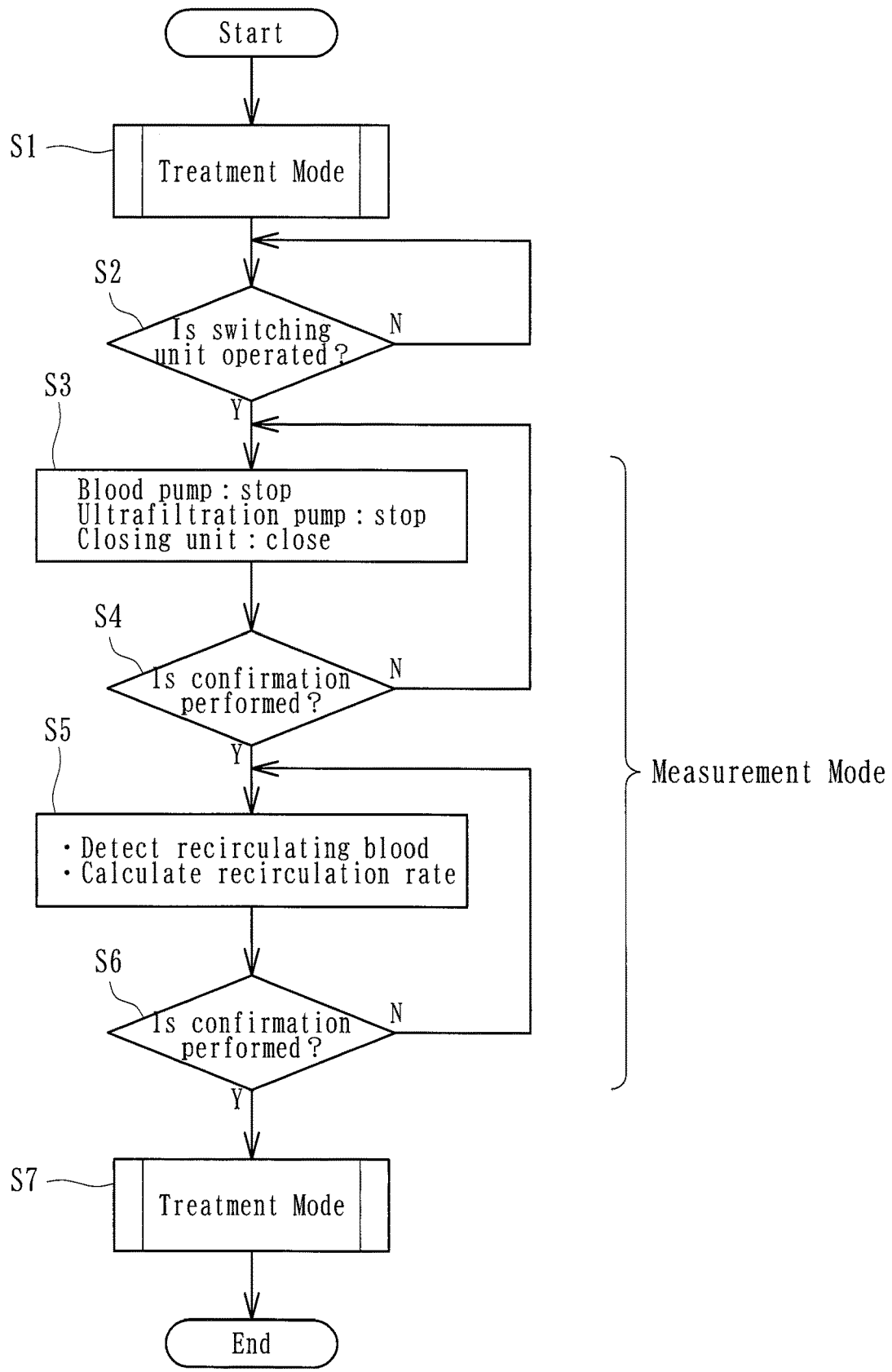
[Fig. 8]

[Fig. 9]
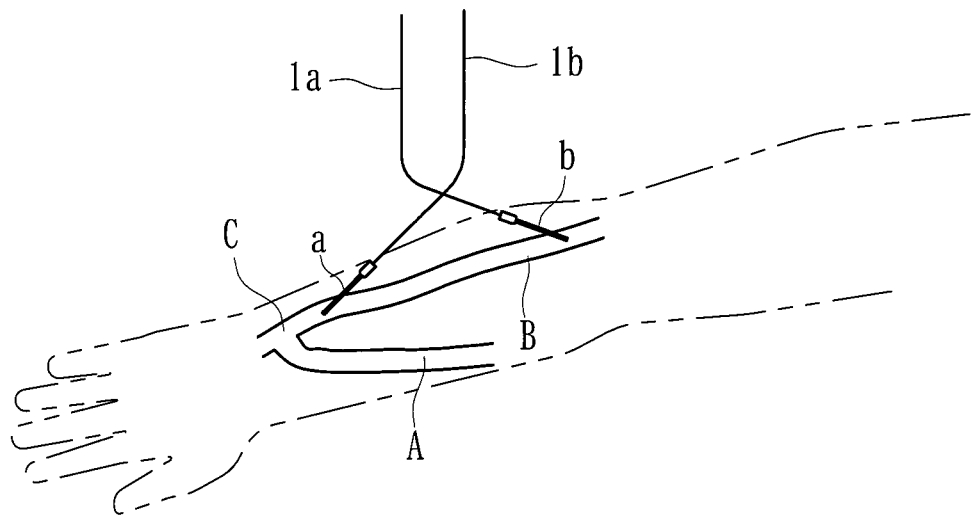
[Fig. 10]
(a)
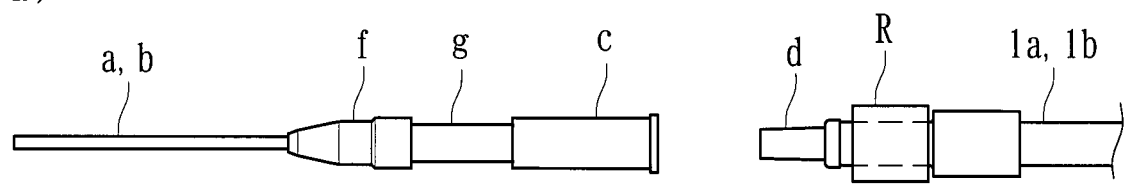
(b)
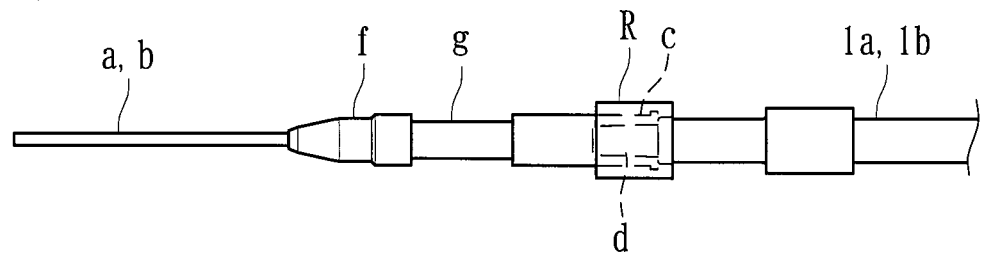

BLOOD PURIFICATION APPARATUS

CROSS-REFERENCE TO RELATED APPLICATION(S)

This application is a continuation of International Application No. PCT/JP2019/016899, filed on Apr. 19, 2019, which claims priority to Japanese Application No. 2018-085075, filed on Apr. 26, 2018, the entire disclosures of which are hereby incorporated by reference.

FIELD

The present teachings relate to a blood purification apparatus capable of performing blood purification treatment with a blood purifier while causing blood of a patient to extracorporeally circulate through a blood circuit by normally rotating a blood pump in a state where an access vessel of the patient is punctured with an arterial puncture needle and a venous puncture needle.

BACKGROUND

In general, blood purification treatment such as dialysis treatment is performed by using a blood circuit formed of flexible tubes so that blood of a patient is caused to extracorporeally circulate. The blood circuit includes an arterial blood circuit provided at a distal end thereof with an arterial puncture needle for collecting blood from a patient, and a venous blood circuit provided at a distal end thereof with a venous puncture needle for returning the blood to the patient. A dialyzer is connected to the arterial blood circuit and to the venous blood circuit, and a blood pump is provided to the arterial blood circuit, whereby blood purification treatment can be performed while the blood is caused to extracorporeally circulate.

To perform blood purification treatment, the patient's blood needs to be caused to extracorporeally circulate by puncturing the patient's access vessel with the arterial puncture needle and the venous puncture needle. If the flow rate in the access vessel is higher than the flow rate of the extracorporeal circulation, the arterial blood circuit (the blood circuit for blood removal) goes under negative pressure. Such a situation leads to a problem that the discharge rate of the blood pump is reduced or a problem of access recirculation in which the blood once returned to the patient's body from the venous puncture needle is recollected into the arterial puncture needle so as to compensate for the insufficiency in the volume of extracorporeal circulation. Consequently, the efficiency of the blood purification treatment is reduced.

To avoid the above problem, it is considered extremely important to accurately calculate the flow rate in the access vessel during the extracorporeal circulation of the blood. For the measurement of the flow rate in the access vessel, a technique has been proposed in which, for example, the arterial puncture needle and the venous puncture needle with which the access vessel is to be punctured are switched therebetween, opposite to the way of puncture for blood purification treatment (see PTL 1). In the above known technique, an upstream part of the access vessel is punctured with the venous puncture needle, and a downstream part of the access vessel is punctured with the arterial puncture needle. In this state, the concentration of the blood that is in extracorporeal circulation is changed. Thus, access flow rate can be measured.

PTL 1: JPH10-505766 (a Published Japanese Translation of a PCT Application), the teachings of which are expressly incorporated by reference herein for all purposes.

SUMMARY

However, the above known technique has the following problem.

To measure the blood flow rate in the access vessel, it is necessary to suspend the dialysis treatment by stopping an ultrafiltration pump and so forth and then to change the state of connection from normal connection in which the upstream part of the access vessel is punctured with the arterial puncture needle and the downstream part of the access vessel is punctured with the venous puncture needle to reverse connection in which the downstream part of the access vessel is punctured with the arterial puncture needle and the upstream part of the access vessel is punctured with the venous puncture needle. That is, to measure the blood flow rate in the access vessel, a medical worker needs to manually switch the state of connection from normal connection to reverse connection. Furthermore, after the flow rate in the access vessel is measured, the medical worker needs to manually reswitch the state of connection from reverse connection to normal connection.

That is, the blood purification apparatus does not recognize a state where the measurement of the blood flow rate in the access vessel is underway. Therefore, the blood purification apparatus cannot inform whether the state of connection of the puncture needles has assuredly been switched or not. Moreover, a medical worker other than the worker who has switched the state of connection of the puncture needles cannot recognize the state where the measurement of the blood flow rate in the access vessel is underway and may therefore misrecognize that the dialysis treatment is underway.

The present invention has been conceived in view of the above circumstances and provides a blood purification apparatus capable of assuredly recognizing that the measurement of the blood flow rate in the access vessel is underway, and also capable of easily and clearly informing that the measurement of the blood flow rate in the access vessel is underway to any medical worker other than a worker who has switched the state of connection of puncture needles.

According to Variation 1, there is provided a blood purification apparatus that includes a blood circuit including an arterial blood circuit provided with an arterial puncture needle with which an access vessel of a patient is puncturable and a venous blood circuit provided with a venous puncture needle with which the access vessel is puncturable, the blood circuit allowing blood of the patient to extracorporeally circulate; a blood purifier connected to the arterial blood circuit and to the venous blood circuit and that purifies the blood flowing through the blood circuit; a blood pump provided to the arterial blood circuit; a recirculating-blood-detecting unit capable of detecting recirculating blood when the blood of the patient is caused to extracorporeally circulate through the blood circuit by activating the blood pump, the recirculating blood being blood once returned to the patient from the venous blood circuit and reintroduced into the arterial blood circuit; and a recirculation-rate-calculating unit capable of calculating recirculation rate, the recirculation rate being a proportion of the recirculating blood in the blood flowing in the arterial blood circuit. The blood purification apparatus includes a control unit capable of executing a treatment mode in which blood purification treatment is performed with the blood purifier while the blood of the patient is caused to extracorporeally circulate through the blood circuit by activating the blood pump in a state of normal connection where an upstream part of the access vessel is punctured with the puncture needle at a distal end of the arterial blood circuit and a downstream part of the access vessel is punctured with the puncture needle at a distal end of the venous blood circuit; and a measurement mode in which the detection of recirculating blood by the recirculating-blood-detecting unit and the calculation of recirculation rate by the recirculation-rate-calculating unit are performed while the blood of the patient is caused to extracorporeally circulate through the blood circuit by activating the blood pump in a state of reverse connection where the downstream part of the access vessel is punctured with the puncture needle at the distal end of the arterial blood circuit and the upstream part of the access vessel is punctured with the puncture needle at the distal end of the venous blood circuit, the calculated recirculation rate being used in calculating blood flow rate in the access vessel that is calculable in the measurement mode.

Variation 2 may comprise the blood purification apparatus according to Variation 1 further includes an index-changing unit that gives a change to an index of the blood extracorporeally circulating through the blood circuit. Furthermore, the detection of recirculating blood by the recirculating-blood-detecting unit and the calculation of recirculation rate by the recirculation-rate-calculating unit are performed in accordance with the change given to the index of the blood from the index-changing unit.

Variation 3 may comprise the blood purification apparatus according to Variation 1 or 2 further includes a switching unit for switching the mode from the treatment mode to the measurement mode.

Variation 4 may comprise the blood purification apparatus according to variation 3 further includes an arterial closing unit capable of closing a distal portion of the arterial blood circuit to block a flow route; and a venous closing unit capable of closing a distal portion of the venous blood circuit to block a flow route. Furthermore, the arterial closing unit and the venous closing unit are openable and closable by the control unit. Furthermore, if the switching unit is operated, the control unit stops the blood pump and causes the arterial closing unit and/or the venous closing unit to close the distal portion of the arterial blood circuit and/or the distal portion of the venous blood circuit.

Variation 5 may comprise the blood purification apparatus according to variation 4 further comprises an ultrafiltration pump for removing water from the blood flowing in the blood purifier. Furthermore, the control unit controls an operation of the ultrafiltration pump. Furthermore, if the switching unit is operated, the control unit stops the blood pump and the ultrafiltration pump.

Variation 6 may comprise the blood purification apparatus according to any of variations 1 to 5, comprising: if the recirculation rate calculated by the recirculation-rate-calculating unit in the treatment mode is higher than a predetermined value or if venous pressure as a hydraulic pressure of the blood flowing in the venous blood circuit in the treatment mode is higher than a predetermined value, it is enabled to provide corresponding information or to prevent the switching from the treatment mode to the measurement mode.

Variation 7 may comprise the blood purification apparatus according to any of variations 1 to 6, comprising in the measurement mode, if reverse-connection confirmation that is enabled after the state of reverse connection is confirmed is performed, the blood flow rate in the access vessel is calculated by causing the recirculating-blood-detecting unit to detect recirculating blood and the recirculation-rate-calculating unit to calculate recirculation rate. Furthermore, if normal-connection confirmation that is enabled after the state of normal connection is confirmed is performed, it is enabled to switch the mode from the measurement mode to the treatment mode.

Variation 8 may comprise the blood purification apparatus according to any of variations 1 to 7, comprising in the treatment mode, the recirculating-blood-detecting unit is caused to detect recirculating blood and the recirculation-rate-calculating unit is caused to calculate recirculation rate. Furthermore, if the mode once switched from the treatment mode to the measurement mode is reswitched to the treatment mode, it is enabled to compare a recirculation rate calculated in an earlier treatment mode and a recirculation rate calculated in a later treatment mode and to judge whether the state of normal connection is appropriate or not.

Variation 9 may comprise in the blood purification apparatus according to any of variations 1 to 7, comprising in the treatment mode, venous pressure as a hydraulic pressure of the blood flowing in the venous blood circuit is detected. Furthermore, if the mode once switched from the treatment mode to the measurement mode is reswitched to the treatment mode, it is enabled to compare a venous pressure detected in an earlier treatment mode and a venous pressure detected in a later treatment mode and to judge whether the state of normal connection is appropriate or not.

Variation 10 may comprise in the blood purification apparatus according to any of variations 1 to 7, comprising in the treatment mode, circulating-blood-volume rate of change calculable from blood concentration that changes with ultrafiltration is detected. Furthermore, after the mode is switched from the measurement mode to the treatment mode, it is enabled to judge whether the state of normal connection is appropriate or not in accordance with a change in the circulating-blood-volume rate of change.

Variation 11 may comprise in the blood purification apparatus according to variation 1 or any of variations 1 to 10, comprising the blood purification apparatus includes the control unit capable of executing the treatment mode in which blood purification treatment is performed with the blood purifier while blood of the patient is caused to extracorporeally circulate through the blood circuit by activating the blood pump in the state of normal connection, and the measurement mode in which the detection of recirculating blood by the recirculating-blood-detecting unit and the calculation of recirculation rate by the recirculation-rate-calculating unit are performed while blood of the patient is caused to extracorporeally circulate through the blood circuit by activating the blood pump in the state of reverse connection, the calculated recirculation rate being used in calculating blood flow rate in the access vessel that is calculable in the measurement mode. Therefore, the apparatus can assuredly recognize that the measurement of the blood flow rate in the access vessel is underway and can also easily and clearly inform that the measurement of the blood flow rate in the access vessel is underway to any medical worker other than a worker who has switched the state of connection of the puncture needles.

Variation 12 may comprise in the blood purification apparatus according to variation 2 or any of variations 1 to 11, comprising the blood purification apparatus further includes the index-changing unit that gives a change to the index of the blood extracorporeally circulating through the blood circuit. Furthermore, the detection of recirculating blood by the recirculating-blood-detecting unit and the calculation of recirculation rate by the recirculation-rate-calculating unit are performed in accordance with the change given to the index of the blood from the index-changing unit. Therefore, the calculation of recirculation rate can be performed at any timing and with high accuracy.

Variation 13 may comprise in the blood purification apparatus according to variation 3 or any of variations 1 to 12, comprising the blood purification apparatus further includes the switching unit for switching the mode from the treatment mode to the measurement mode. Therefore, the switching to the measurement mode can be performed easily and assuredly.

Variation 14 may comprise in the blood purification apparatus according to variation 4 or any of variations 1 to 13, comprising the arterial closing unit and the venous closing unit are openable and closable by the control unit. Furthermore, if the switching unit is operated, the control unit stops the blood pump and causes the arterial closing unit and/or the venous closing unit to close the distal portion of the arterial blood circuit and/or the distal portion of the venous blood circuit, respectively. Therefore, blood leakage from the distal portion of the arterial blood circuit and the distal portion of the venous blood circuit in the measurement mode can be prevented assuredly.

Variation 15 may comprise in the blood purification apparatus according to variation 5 or any of variations 1 to 14, comprising the control unit controls the operation of the ultrafiltration pump. Furthermore, if the switching unit is operated, the control unit stops the blood pump and the ultrafiltration pump. Therefore, in the measurement mode, the patient's blood can be assuredly prevented from being ultrafiltered.

Variation 16 may comprise in the blood purification apparatus according to variation 6 or any of variations 1 to 15, comprising if the recirculation rate calculated in the treatment mode by the recirculation-rate-calculating unit is higher than a predetermined value or if the venous pressure as the hydraulic pressure of the blood flowing in the venous blood circuit in the treatment mode is higher than a predetermined value, it is enabled to provide corresponding information or to prevent the switching from the treatment mode to the measurement mode. Therefore, the safety of the patient at the switching to the measurement mode can be increased.

Variation 17 may comprise in the blood purification apparatus according to variation 7 or any of variations 1 to 16, comprising in the measurement mode, if reverse-connection confirmation that is enabled after the state of reverse connection is confirmed is performed, blood flow rate in the access vessel is calculated by causing the recirculating-blood-detecting unit to detect recirculating blood and the recirculation-rate-calculating unit to calculate recirculation rate. Furthermore, if normal-connection confirmation that is enabled after the state of normal connection is confirmed is performed, it is enabled to switch the mode from the measurement mode to the treatment mode. Therefore, the measurement of the blood flow rate in the access vessel can be performed after the confirmation of the state of reverse connection, and the switching to the treatment mode can be performed after the confirmation of the state of normal connection.

Variation 18 may comprise in the blood purification apparatus according to variation 8 or any of variations 1 to 17, comprising in the treatment mode, the recirculating-blood-detecting unit is caused to detect recirculating blood, and the recirculation-rate-calculating unit is caused to calculate recirculation rate. Furthermore, if the mode once switched from the treatment mode to the measurement mode is reswitched to the treatment mode, it is enabled to compare the recirculation rate calculated in the earlier treatment mode and the recirculation rate calculated in the later treatment mode and to judge whether the state of normal connection is appropriate or not. Therefore, the judgement of the state of connection in the treatment mode can be made by using the recirculation rates calculated in the treatment mode.

Variation 19 may comprise in the blood purification apparatus according to variation 9 or any of variations 1 to 18, comprising in the treatment mode, venous pressure as the hydraulic pressure of blood flowing in the venous blood circuit is detected. Furthermore, if the mode once switched from the treatment mode to the measurement mode is reswitched to the treatment mode, it is enabled to compare the venous pressure detected in the earlier treatment mode and the venous pressure detected in the later treatment mode and to judge whether the state of normal connection is appropriate or not. Therefore, the judgement of the state of connection in the treatment mode can be made by using the venous pressures detected in the treatment mode.

Variation 20 may comprise in the blood purification apparatus according to variation 10 or any of variations 1 to 19, comprising circulating-blood-volume rate of change calculable from blood concentration that changes with ultrafiltration is detected. Furthermore, after the mode is switched from the measurement mode to the treatment mode, it is enabled to judge whether the state of normal connection is appropriate or not in accordance with the change in the circulating-blood-volume rate of change. Therefore, the judgement of the state of connection in the treatment mode can be made by using the circulating-blood-volume rate of change detected in the treatment mode.

BRIEF DESCRIPTION OF THE DRAWINGS

FIG. 1 is an overall diagram of a blood purification apparatus according to an embodiment of the present invention.

FIG. 2 is a diagram illustrating a state of normal connection of an arterial puncture needle and a venous puncture needle included in the blood purification apparatus.

FIG. 3 is a diagram illustrating a state of reverse connection of the arterial puncture needle and the venous puncture needle included in the blood purification apparatus.

FIG. 4 is a graph illustrating a specific change given by the blood purification apparatus (in a case where the blood concentration is increased).

FIG. 5 is a graph illustrating a specific change detected by the blood purification apparatus (in the case where the blood concentration is increased).

FIG. 6 is a graph illustrating a specific change given by the blood purification apparatus (in a case where the blood concentration is reduced).

FIG. 7 is a graph illustrating a specific change detected by the blood purification apparatus (in the case where the blood concentration is reduced).

FIG. 8 is a flow chart of a control process executed by a control unit of the blood purification apparatus.

FIG. 9 is a diagram illustrating a state of reverse connection of the arterial puncture needle and the venous puncture needle included in the blood purification apparatus (a state where an arterial blood circuit and a venous blood circuit are switched therebetween by switching the state of connection of the blood circuit from normal connection to reverse connection while the puncture needles are kept in a puncturing state).

FIG. 10 includes diagrams each illustrating the puncture needle to be attached to a distal end of the arterial blood circuit or the venous blood circuit of the blood purification apparatus, with (a) illustrating the puncture needle removed from the distal end of the arterial blood circuit or the venous blood circuit and (b) illustrating the puncture needle attached to the distal end of the arterial blood circuit or the venous blood circuit.

DETAILED DESCRIPTION

Embodiments of the present teachings will now be described specifically with reference to the drawings.

A blood purification apparatus according to the present embodiment is a dialysis apparatus intended for dialysis treatment and includes, as illustrated in FIG. 1, a blood circuit 1 including an arterial blood circuit 1a provided with an arterial puncture needle (a) at a distal end thereof and a venous blood circuit 1b provided with a venous puncture needle (b) at a distal end thereof, the blood circuit 1 allowing blood of a patient to extracorporeally circulate; a dialyzer 2 (a blood purifier) connected to the arterial blood circuit 1a and to the venous blood circuit 1b and that purifies the blood flowing through the blood circuit 1; a blood pump 3 provided to the arterial blood circuit 1a; an arterial air-trap chamber 4 and a venous air-trap chamber 5 connected to the arterial blood circuit 1a and the venous blood circuit 1b, respectively; a duplex pump 6; an ultrafiltration pump 7; a venous pressure sensor 10; a recirculation-rate-calculating unit 11; a control unit 12; a switching unit 13; a confirming unit 14; an informing unit 15; a judging unit 16; a first detecting unit E1 and a second detecting unit E2 that serve as a recirculating-blood-detecting unit; a dialysate introduction line L1 through which dialysate is introduced into the dialyzer 2; and a dialysate drain line L2 through which waste liquid is drained from the dialyzer 2.

The arterial blood circuit 1a (for blood removal) is provided with a connector at the distal end thereof. The arterial puncture needle (a) is connectable to the arterial blood circuit 1a through the connector. The blood pump 3, which is of a peristaltic type, and the arterial air-trap chamber 4 are provided at respective halfway positions of the arterial blood circuit 1a. The venous blood circuit 1b (for blood return) is provided with a connector at the distal end thereof. The venous puncture needle (b) is connectable to the venous blood circuit 1b through the connector. The venous air-trap chamber 5 is provided at a halfway position of the venous blood circuit 1b.

The arterial blood circuit 1a is provided with an arterial closing unit Va capable of closing a distal portion thereof to block the flow route. The venous blood circuit 1b is provided with a venous closing unit Vb capable of closing a distal portion thereof to block the flow route. The arterial closing unit Va and the venous closing unit Vb are each a clamping unit, an electromagnetic valve, or the like. To perform blood purification treatment, the arterial closing unit Va and the venous closing unit Vb are opened to allow the blood to extracorporeally circulate through the blood circuit 1. In this specification, the side of the puncture needle for blood removal (blood collection) is referred to as the "arterial" side, and the side of the puncture needle for blood return is referred to as the "venous" side. The "arterial" side and the "venous" side are not defined in accordance with which of the artery and the vein is to be the object of puncture.

The arterial puncture needle (a) and the venous puncture needle (b) may each be a hemodialysis winged needle having wing-shaped parts to be brought into close contact with the patient for keeping the puncture needle in a puncturing state. The arterial puncture needle (a) and the venous puncture needle (b) according to the present embodiment are each a metal needle (such as the hemodialysis winged needle or the like) but are not limited thereto. For example, the arterial puncture needle (a) and the venous puncture needle (b) may each be a hemodialysis trocar catheter (see an indwelling-needle body illustrated in FIG. 10).

When the blood pump 3 is activated (rotated normally) while the patient is punctured with the arterial puncture needle (a) connected to the distal end of the arterial blood circuit 1a and with the venous puncture needle (b) connected to the distal end of the venous blood circuit 1b, blood of the patient flows through the arterial blood circuit 1a while undergoing bubble removal in the arterial air-trap chamber 4 and reaches the dialyzer 2, where the blood is purified. Then, the blood flows through the venous blood circuit 1b while undergoing bubble removal in the venous air-trap chamber 5 and returns into the patient's body. Thus, the patient's blood can be purified with the dialyzer 2 while the blood is caused to extracorporeally circulate through the blood circuit 1 from the distal end of the arterial blood circuit 1a to the distal end of the venous blood circuit 1b.

The dialyzer 2 has, in a housing thereof, a blood inlet 2a (a blood introduction port), a blood outlet 2b (a blood delivery port), a dialysate inlet 2c (an inlet of a dialysate flow route, a dialysate introduction port), and a dialysate outlet 2d (an outlet of the dialysate flow route, a dialysate delivery port). The blood inlet 2a is connected to the arterial blood circuit 1a. The blood outlet 2b is connected to the venous blood circuit 1b. The dialysate inlet 2c and the dialysate outlet 2d are connected to the dialysate introduction line L1 and the dialysate drain line L2, respectively.

The dialyzer 2 houses a plurality of hollow fiber membranes (not illustrated) formed of hollow fibers, serving as blood purification membranes for purifying the blood. The blood purification membranes in the dialyzer 2 define blood flow routes (each extending between the blood inlet 2a and the blood outlet 2b) through which the patient's blood flows and dialysate flow routes (each extending between the dialysate inlet 2c and the dialysate outlet 2d) through which dialysate flows. The hollow fiber membranes forming the blood purification membranes each have a number of microscopic holes (pores) extending therethrough from the outer peripheral surface to the inner peripheral surface. Impurities and the like contained in the blood are allowed to permeate through the hollow fiber membranes into the dialysate.

The venous air-trap chamber 5 is provided with the venous pressure sensor 10 capable of detecting the hydraulic pressure in the venous blood circuit 1b (venous pressure) by detecting the pressure in an air layer formed on the upper side thereof while the blood is extracorporeally circulating through the blood circuit 1. That is, venous pressure as the hydraulic pressure of the blood flowing in the venous blood circuit 1b can be detected by the venous pressure sensor 10. Hence, when the blood purification treatment is started and the patient's blood is caused to extracorporeally circulate through the blood circuit 1, the venous pressure detected by the venous pressure sensor 10 can be monitored.

The arterial blood circuit 1a and the venous blood circuit 1b according to the present embodiment are each provided on the distal portion thereof with a bubble detector (D1, D2) capable of detecting gas (bubbles) contained in the blood flowing in the arterial blood circuit 1a or the venous blood circuit 1b during the blood purification treatment. The bubble detector (D1, D2) is a sensor capable of detecting bubbles (air) flowing in a flexible tube forming the arterial blood circuit 1*a* or the venous blood circuit 1*b*, and includes, for example, an ultrasonic vibrator formed of a piezoelectric device and an ultrasonic receiver formed of a piezoelectric device. The bubble detector (D1, D2) is capable of emitting ultrasonic waves from the ultrasonic vibrator toward the flexible tube forming the arterial blood circuit 1*a* or the venous blood circuit 1*b*, and is also capable of receiving the thus generated vibration by the ultrasonic receiver.

The ultrasonic receiver generates a voltage that changes with the vibration received. The ultrasonic receiver is capable of detecting the flow of bubbles by a fact that the detected voltage has exceeded a predetermined threshold. Specifically, the ultrasonic attenuation factor of bubbles is higher than those of blood and substitution solutions. Hence, if the voltage detected by the ultrasonic receiver has exceeded the predetermined threshold, it is regarded that the flow of bubbles (gas) has been detected.

The first detecting unit E1 is a hematocrit sensor attached to a predetermined site of the arterial blood circuit 1*a* (in the present embodiment, between the position where the blood pump 3 is provided and the position where the arterial air-trap chamber 4 is connected). The first detecting unit E1 is capable of detecting the concentration of the blood flowing in the blood circuit 1 (the arterial blood circuit 1*a*) during the blood purification treatment. The second detecting unit E2 is a hematocrit sensor attached to a predetermined site of the venous blood circuit 1*b* (in the present embodiment, between the position where the bubble detector D2 is provided and the position where the venous air-trap chamber 5 is connected). The second detecting unit E2 is capable of detecting the concentration of the blood flowing in the blood circuit 1 (the venous blood circuit 1*b*) during the blood purification treatment.

More specifically, the first detecting unit E1 and the second detecting unit E2 according to the present embodiment each include a pair of light-emitting device and a light-receiving device. The light-emitting device is, for example, an LED capable of emitting near infrared rays (a near-infrared LED). The light-receiving device is a photodiode. When the light-emitting device emits light, the light strikes the flexible tube forming the arterial blood circuit 1*a* or the venous blood circuit 1*b* and is reflected by the blood flowing thereinside. Then, the reflected light is received by the light-receiving device (a configuration of a so-called reflection sensor).

In accordance with a voltage generated at the light reception by the light-receiving device, hematocrit value indicating blood concentration can be calculated. Specifically, blood components, such as red blood cells and plasma, each have an inherent absorption characteristic. Using the absorption characteristics of such components, hematocrit value is calculable by electrooptically quantifying the amount of red blood cells required for the measurement of hematocrit value. In the present embodiment, the first detecting unit E1 and the second detecting unit E2 are each a so-called reflection sensor as described above. Alternatively, hematocrit value (blood concentration) may be measured in accordance with the voltage generated when the light emitted from the light-emitting device and transmitted through the blood is received by the light-receiving device.

The dialysate introduction line L1 and the dialysate drain line L2 are provided with the duplex pump 6. The duplex pump 6 delivers dialysate prepared at a predetermined concentration to the dialyzer 2 and drains the dialysate and waste products and the like (waste liquid) from the dialyzer 2. Specifically, the duplex pump 6 is provided over the dialysate introduction line L1 and the dialysate drain line L2.

When the duplex pump 6 is activated, the dialysate can be introduced into the dialyzer 2 through the dialysate introduction line L1 and drained from the dialyzer 2 through the dialysate drain line L2.

The dialysate introduction line L1 is provided with electromagnetic valves V1 and V3 and filters F1 and F2. The dialysate to be introduced into the dialyzer 2 can be filtered by the filters F1 and F2. The flow route can be blocked or opened by the electromagnetic valves V1 and V3 at any timing. The dialysate introduction line L1 is connected to the dialysate drain line L2 through bypass lines L4 and L5. The bypass lines L4 and L5 are provided with electromagnetic valves V4 and V5, respectively. The dialysate introduction line L1 is also provided with a heating unit H, so that the dialysate can be heated to any temperature.

The dialysate drain line L2 is provided with detour lines L3 and L6 each detouring the duplex pump 6. The detour line L6 is provided with an electromagnetic valve V6. The detour line L3 is provided with the ultrafiltration pump 7. When the ultrafiltration pump 7 is activated in the process of causing the patient's blood to extracorporeally circulate through the blood circuit 1, ultrafiltration can be performed in which water is removed from the blood flowing in the dialyzer 2.

The dialysate drain line L2 is provided with a pressurizing pump 8 at a position on the upstream side (the left side in FIG. 1) with respect to the duplex pump 6. The pressurizing pump 8 adjusts the hydraulic pressure in the dialysate drain line L2 at the duplex pump 6. The dialysate drain line L2 is further provided with a release line L7 extending from a degassing chamber 9 provided between the pressurizing pump 8 and the duplex pump 6. The dialysate drain line L2 and the release line L7 branching off therefrom are provided with electromagnetic valves V2 and V7, respectively, so that the flow route for the dialysate can be blocked or opened at any timing.

Furthermore, the blood purification apparatus according to the present embodiment includes an index-changing unit that gives a specific change to an index of the blood extracorporeally circulating through the blood circuit 1. The index-changing unit may be, for example, the ultrafiltration pump 7, a combination of the release line L7 and the electromagnetic valve V7, or the duplex pump 6. If the ultrafiltration pump 7 is used as the index-changing unit, the ultrafiltration pump 7 is rapidly driven for a short time with the electromagnetic valves V1 to V3 open but the electromagnetic valves V4 to V7 closed, whereby short-time and rapid ultrafiltration of the blood flowing in the blood flow routes in the dialyzer 2 is performed to instantly concentrate the blood. Thus, as illustrated in FIG. 4, the blood concentration as a blood index can be instantly increased to exhibit a specific change (Sv) (that is, the blood index can be changed).

If the combination of the release line L7 and the electromagnetic valve V7 is used as the index-changing unit, the electromagnetic valve V7 is opened for a short time with the electromagnetic valves V1 to V3 open but the electromagnetic valves V4 to V6 closed so that the discharge pressure of the pressurizing pump 8 is set to the atmospheric pressure, whereby short-time and rapid ultrafiltration of the blood flowing in the blood flow routes in the dialyzer 2 is performed to instantly concentrate the blood. Thus, as illustrated in FIG. 4, the blood concentration as a blood index can be instantly increased to exhibit a specific change (Sv).

If the duplex pump 6 is used as the index-changing unit, the duplex pump 6 is rapidly driven for a short time with the electromagnetic valves V1, V3, and V6 open but the electromagnetic valves V2, V4, and V5 closed, whereby short-time and rapid injection of the dialysate into the blood flowing in the blood flow routes in the dialyzer 2 is performed to instantly dilute the blood. Thus, as illustrated in FIG. 6, the blood concentration as a blood index can be instantly reduced to exhibit a specific change (Sv).

In a treatment mode where blood purification treatment is performed with the dialyzer 2 while blood of the patient is caused to extracorporeally circulate through the blood circuit 1, as illustrated in FIG. 2, an upstream part of an access vessel (a part near a shunt site C where an artery A and a vein B are connected) is punctured with the arterial puncture needle (a), and a downstream part of the access vessel (a part of the vein B that is on the downstream side with respect to the part near the shunt site C) is punctured with the venous puncture needle (b). The access vessel is a blood vessel called shunt (the shunt site C above) where an artery and a vein are connected by any method such as surgery. Normally, the shunt is punctured with puncture needles to perform dialysis treatment. Shunts include an AVF provided by direct inosculation of an artery and a subcutaneous vein, and an AVG provided by bypassing between an artery and a vein with a synthetic blood vessel.

In the treatment mode, the blood pump 3 is activated in a state of normal connection where the upstream part of the access vessel is punctured with the puncture needle (the arterial puncture needle (a)) at the distal end of the arterial blood circuit 1a and the downstream part of the access vessel is punctured with the puncture needle (the venous puncture needle (b)) at the distal end of the venous blood circuit 1b. Accordingly, blood given a specific change from the index-changing unit can be made to flow into the access vessel. Hence, if there is any recirculating blood, the second detecting unit E2 detects a specific change (Sv) illustrated in FIG. 4 or 6 and the first detecting unit E1 detects a specific change (Sa), illustrated in FIG. 5 or 7, which is diluted (weakened) with the blood flowing in the access vessel.

As described above, the first detecting unit E1 and the second detecting unit E2 according to the present embodiment are each capable of detecting a specific change (a specific change in the blood concentration) given by the index-changing unit, and serve as the recirculating-blood-detecting unit capable of detecting recirculating blood when blood of the patient is caused to extracorporeally circulate through the blood circuit 1 by activating the blood pump 3. Recirculating blood is blood once returned to the patient from the venous blood circuit 1b and reintroduced into the arterial blood circuit 1a.

The recirculation-rate-calculating unit 11 is capable of calculating recirculation rate, which is the proportion of recirculating blood in the blood flowing in the arterial blood circuit 1a. The recirculation-rate-calculating unit 11 calculates the proportion of recirculating blood (recirculation rate) in the treatment mode in accordance with the change in the blood index detected by the recirculating-blood-detecting unit (the first detecting unit E1 and the second detecting unit E2). The recirculation-rate-calculating unit 11 is capable of calculating recirculation rate (RR) as the proportion of recirculating blood in accordance with, for example, a mathematical expression Sa/Sv×100, which is the area ratio between Sa and Sv.

The blood purification apparatus according to the present embodiment includes the control unit 12 capable of executing not only the treatment mode in which, as described above, blood purification treatment is performed with the dialyzer 2 while blood of the patient is caused to extracorporeally circulate through the blood circuit 1 by activating the blood pump 3 in the state of normal connection where the upstream part of the access vessel is punctured with the puncture needle (the arterial puncture needle (a)) at the distal end of the arterial blood circuit 1a and the downstream part of the access vessel is punctured with the puncture needle (the venous puncture needle (b)) at the distal end of the venous blood circuit 1b, but also a measurement mode in which, as illustrated in FIG. 3, the detection of recirculating blood by the recirculating-blood-detecting unit (the first detecting unit E1 and the second detecting unit E2) and the calculation of recirculation rate (RR) by the recirculation-rate-calculating unit 11 are performed while blood of the patient is caused to extracorporeally circulate through the blood circuit 1 by activating the blood pump 3 in a state of reverse connection where the downstream part of the access vessel is punctured with the puncture needle (the arterial puncture needle (a)) at the distal end of the arterial blood circuit 1a and the upstream part of the access vessel is punctured with the puncture needle (the venous puncture needle (b)) at the distal end of the venous blood circuit 1b, the calculated recirculation rate (RR) being used in calculating access-vessel blood flow rate (Qa) that is calculable in the measurement mode.

To execute the measurement mode, a medical worker manually removes the arterial puncture needle (a) and the venous puncture needle (b) that are in normal connection and then establishes the state of reverse connection where the downstream part of the access vessel is punctured with the arterial puncture needle (a) and the upstream part of the access vessel is punctured with the venous puncture needle (b). When the measurement mode is executed, since the blood pump 3 is activated in the state of reverse connection, blood given a specific change from the index-changing unit can be made to flow into the access vessel. Accordingly, the second detecting unit E2 detects the specific change (Sv), illustrated in FIG. 4 or 6, and the first detecting unit E1 detects the specific change (Sa), illustrated in FIG. 5 or 7, which is diluted (weakened) with the blood flowing in the access vessel. Thus, recirculating blood as the blood once returned to the patient from the venous blood circuit 1b and reintroduced into the arterial blood circuit 1a is detected.

As described above, the recirculation-rate-calculating unit 11 is capable of calculating recirculation rate as the proportion of recirculating blood in the blood flowing in the arterial blood circuit 1a. The recirculation-rate-calculating unit 11 calculates the proportion of recirculating blood (recirculation rate) in the measurement mode in accordance with the change in the blood index detected by the recirculating-blood-detecting unit (the first detecting unit E1 and the second detecting unit E2). As with the case of the treatment mode, the recirculation-rate-calculating unit 11 is capable of calculating recirculation rate (RR) as the proportion of recirculating blood in accordance with, for example, a mathematical expression Sa/Sv×100, which is the area ratio between Sa and Sv.

After the detection of recirculating blood by the recirculating-blood-detecting unit (the first detecting unit E1 and the second detecting unit E2) and the calculation of recirculation rate RR by the recirculation-rate-calculating unit 11, access-vessel blood flow rate (Qa) can be calculated in accordance with the calculated recirculation rate (RR). Specifically, when blood given a specific change from the index-changing unit is made to flow into the access vessel by activating the blood pump 3, the flow rate of the blood in the access vessel is reduced to Qb/(Qa+Qb). Therefore, the ratio (Sa/Sv) between the area of the specific change given from the index-changing unit (that is, the area of the specific change Sv detected by the second detecting unit E2) and the area of the specific change (Sa) detected by the first detecting unit E1 is equal to Qb/(Qa+Qb). Hence, letting the blood flow rate in the access vessel be Qa and the flow rate at the activation of the blood pump 3 (or the blood flow rate in the blood circuit 1) be Qb, a mathematical expression Qa=Qb (Sa/Sv−1) is obtained. In accordance with this expression, access-vessel blood flow rate (Qa) can be calculated.

As described above, when the measurement mode is executed by the control unit 12, access-vessel blood flow rate (Qa) can be calculated. Therefore, if the measurement mode is executed every time the blood purification treatment is performed, the access-vessel blood flow rate (Qa) of the patient can be managed. For example, if the access-vessel blood flow rate (Qa) calculated in the measurement mode is below a predetermined value (for example, 600 mL/min), stenosis of the access vessel may be suspected. Accordingly, an examination of the access vessel, such as angiography, may be conducted.

When the above measurement mode is ended, the medical worker manually removes the arterial puncture needle (a) and the venous puncture needle (b) that are in reverse connection and then establishes the state of normal connection where, as illustrated in FIG. 2, the upstream part of the access vessel is punctured with the arterial puncture needle (a) and the downstream part of the access vessel is punctured with the venous puncture needle (b). Then, the blood pump 3 is activated in the state of normal connection, whereby blood purification treatment is performed with the dialyzer 2 while the patient's blood is caused to extracorporeally circulate through the blood circuit 1.

The blood purification apparatus according to the present embodiment further includes the switching unit 13 for switching the mode from the treatment mode to the measurement mode. The switching unit 13 is displayed on a display, such as a touch panel, included in the blood purification apparatus and is capable of switching the mode from the treatment mode to the measurement mode when touched with a finger of the medical worker. The switching unit 13 is not limited to a device displayed on a display and operable by the touch and may be a physically switchable device such as a push button or an operation lever.

The arterial closing unit Va and the venous closing unit Vb according to the present embodiment are openable and closable by the control unit 12. If the switching unit 13 is operated, the control unit 12 stops the blood pump 3 and causes the arterial closing unit Va and the venous closing unit Vb to close the distal portion of the arterial blood circuit 1a and the distal portion of the venous blood circuit 1b, respectively. Alternatively, if the switching unit 13 is operated, the control unit 12 may stop the blood pump 3 and cause the arterial closing unit Va or the venous closing unit Vb to close the distal portion of the arterial blood circuit 1a or the distal portion of the venous blood circuit 1b.

The operation of the ultrafiltration pump 7 according to the present embodiment is also controlled by the control unit 12. If the switching unit 13 is operated, the control unit 12 stops the ultrafiltration pump 7 as well as the blood pump 3. That is, in the present embodiment, if the switching unit 13 is operated, the control unit 12 stops the blood pump 3 and the ultrafiltration pump 7 and causes the arterial closing unit Va and the venous closing unit Vb to close the distal portion of the arterial blood circuit 1a and the distal portion of the venous blood circuit 1b, respectively.

The blood purification apparatus according to the present embodiment further includes the confirming unit 14 that is operable after the medical worker confirms a predetermined operation or state. The confirming unit 14 is displayed on a display, such as a touch panel, included in the blood purification apparatus. When the confirming unit 14 is touched with a finger of the medical worker, operations to be performed after the confirmation are enabled. The confirming unit 14 is not limited to a device displayed on a display and operable by the touch and may be a physically switchable device such as a push button or an operation lever.

In the present embodiment, reverse-connection confirmation is enabled by operating the confirming unit 14 after the state of reverse connection is confirmed, and normal-connection confirmation is enabled by operating the confirming unit 14 after the state of normal connection is confirmed. Furthermore, in the measurement mode, if reverse-connection confirmation that is enabled after the state of reverse connection is confirmed is performed, access-vessel blood flow rate (Qa) is calculated by causing the recirculating-blood-detecting unit (the first detecting unit E1 and the second detecting unit E2) to detect recirculating blood and the recirculation-rate-calculating unit 11 to calculate recirculation rate. Furthermore, if normal-connection confirmation that is enabled after the state of normal connection is confirmed is performed, it is enabled to switch the mode from the measurement mode to the treatment mode.

In the present embodiment, if the switching unit 13 is operated, the blood pump 3 and the ultrafiltration pump 7 are stopped, and the arterial closing unit Va and the venous closing unit Vb close the distal portion of the arterial blood circuit 1a and the distal portion of the venous blood circuit 1b. Subsequently, the informing unit 15 provides information (for example, a message such as "Do you want to measure recirculation rate?"). Then, if the confirming unit 14 is operated, the recirculation-rate-calculating unit 11 calculates recirculation rate (RR).

The informing unit 15 is a device such as a display (a liquid-crystal display or the like) capable of displaying any information, a speaker capable of outputting any sound such as a voice or a sound effect, or a kind of lamp (an external indicator light) capable of turning on or blinking in any way. For example, in the treatment mode, the speaker does not output any sound, but the external indicator light turns green (if there is no warning or the like). On the other hand, in the measurement mode, a voice or sound effect informing that the measurement of access-vessel blood flow rate is underway is outputted, and the external indicator light blinks in yellow (for example, the light blinks at a frequency of about 1 Hz).

Furthermore, in the measurement mode, a voice providing detailed information for each of relevant processes is outputted. For example, if the switching unit 13 is operated, a voice that prompts to confirm the state of reverse connection and to operate the confirming unit 14 is outputted. If the arterial closing unit Va and the venous closing unit Vb are manually openable and closable, a voice that prompts to check whether the arterial closing unit Va and the venous closing unit Vb are open or closed is outputted. In addition, in the measurement mode, if it is confirmed that the condition of the patient after blood removal is stabilized, a voice that prompts to start the measurement of recirculation rate (RR) may be outputted.

When the measurement of recirculation rate (RR) is started, the display provides corresponding information (for example, a massage such as "Measurement is underway. Please wait for a while."). Then, when the measurement of recirculation rate (RR) is ended, a voice that prompts to confirm the state of normal connection and to operate the confirming unit 14 is outputted. If the arterial closing unit Va and the venous closing unit Vb are manually openable and closable, a voice that prompts to check whether the arterial closing unit Va and the venous closing unit Vb are open or closed is outputted.

Furthermore, in the present embodiment, if the recirculation rate (RR) calculated by the recirculation-rate-calculating unit 11 in the treatment mode is higher than a predetermined value or if the venous pressure as the hydraulic pressure of the blood flowing in the venous blood circuit 1b in the treatment mode (that is, the venous pressure detected by the venous pressure sensor 10) is higher than a predetermined value, the informing unit 15 can provide corresponding information or the switching from the treatment mode to the measurement mode can be prevented.

The judging unit 16 is capable of judging whether the state of normal connection in the treatment mode is appropriate or not. For example, in the treatment mode, the judging unit 16 causes the recirculating-blood-detecting unit (the first detecting unit E1 and the second detecting unit E2) to detect recirculating blood and the recirculation-rate-calculating unit 11 to calculate recirculation rate (RR). Furthermore, if the mode once switched from the treatment mode to the measurement mode is reswitched to the treatment mode, the judging unit 16 can compare the recirculation rate (RR) calculated in the earlier treatment mode and the recirculation rate (RR) calculated in the later treatment mode and judge whether the state of normal connection is appropriate or not. Specifically, if the difference or ratio between the recirculation rate (RR) calculated in the earlier treatment mode and the recirculation rate (RR) calculated in the later treatment mode is greater than or equal to a predetermined value, it is judged that the difference between the two recirculation rates (RRs) is over the estimation. Hence, it can be judged that the state of normal connection is inappropriate.

In the treatment mode, the judging unit 16 may cause the venous pressure sensor 10 to detect venous pressure as the hydraulic pressure of blood flowing in the venous blood circuit 1b. Furthermore, if the mode once switched from the treatment mode to the measurement mode is reswitched to the treatment mode, the judging unit 16 may compare the venous pressure detected in the earlier treatment mode and the venous pressure detected in the later treatment mode and judge whether the state of normal connection is appropriate or not. Specifically, if the difference or ratio between the venous pressure detected in the earlier treatment mode and the venous pressure detected in the later treatment mode is greater than or equal to a predetermined value, it is judged that the difference between the two venous pressures is over the estimation. Hence, it can be judged that the state of normal connection is inappropriate.

Furthermore, in the treatment mode, the judging unit 16 may initiate the detection of circulating-blood-volume rate of change ($\Delta BV$) calculable from blood concentration that changes with the ultrafiltration by the ultrafiltration pump 7. Furthermore, after the mode is switched from the measurement mode to the treatment mode, the judging unit 16 may judge whether the state of normal connection is appropriate or not in accordance with the change in the circulating-blood-volume rate of change ($\Delta BV$). Specifically, circulating-blood-volume rate of change ($\Delta BV$) is calculated from a mathematical expression (hematocrit value (Ht) at start of treatment—hematocrit value (Ht) during measurement)/hematocrit value (Ht) during measurement×100. Normally, circulating-blood-volume rate of change is gradually reduced because ultrafiltration is performed during the treatment. Therefore, if the measured change in the circulating-blood-volume rate of change ($\Delta BV$) is over the estimation, it can be judged that the state of normal connection is inappropriate.

Now, a control process executed by the control unit 12 according to the present embodiment will be described with reference to a flow chart illustrated in FIG. 8.

First, while the treatment mode is underway (S1) by activating the blood pump 3 with the arterial puncture needle (a) and the venous puncture needle (b) being in normal connection, whether the switching unit 13 is operated by an operator or not is checked (S2). If it is judged that the switching unit 13 is operated, the process proceeds to S3, where the blood pump 3 and the ultrafiltration pump 7 are stopped, and the distal portion of the arterial blood circuit 1a and the distal portion of the venous blood circuit 1b are closed by the arterial closing unit Va and the venous closing unit Vb, respectively, whereby the mode is switched to the measurement mode.

In this state, the medical worker manually switches the connection of the arterial puncture needle (a) and the venous puncture needle (b) from normal connection to reverse connection. Then, the informing unit 15 provides information that prompts to check whether the detection of recirculating blood and the calculation of recirculation rate are to be performed or not. Subsequently, whether the confirming unit 14 is operated by the operator or not is checked (S4). If it is judged that the confirming unit 14 is operated, the process proceeds to S5, where the index-changing unit gives a change to the blood index. Then, the detection of recirculating blood by the recirculating-blood-detecting unit and the calculation of recirculation rate by the recirculation-rate-calculating unit 11 are performed.

Subsequently, the informing unit 15 provides information indicating that the measurement of recirculation rate (RR) is ended. Then, it is confirmed that the connection of the arterial puncture needle (a) and the venous puncture needle (b) is switched by the medical worker from reverse connection to normal connection. Furthermore, whether the confirming unit 14 is operated by the operator or not is checked (S6). If it is judged that the confirming unit 14 is operated, the process proceeds to S7, where the treatment mode is executed again.

According to the present embodiment, the blood purification apparatus includes the control unit 12 capable of executing the treatment mode in which blood purification treatment is performed with the dialyzer 2 while blood of the patient is caused to extracorporeally circulate through the blood circuit 1 by activating the blood pump 3 in the state of normal connection, and the measurement mode in which the detection of recirculating blood by the recirculating-blood-detecting unit (the first detecting unit E1 and the second detecting unit E2) and the calculation of recirculation rate (RR) by the recirculation-rate-calculating unit 11 are performed while blood of the patient is caused to extracorporeally circulate through the blood circuit 1 by activating the blood pump 3 in the state of reverse connection, the calculated recirculation rate (RR) being used in calculating access-vessel blood flow rate (Qa) that is calculable in the measurement mode. Therefore, the apparatus can assuredly recognize that the measurement of access-vessel blood flow rate (Qa) is underway and can also easily and clearly inform that the measurement of access-vessel blood flow rate is underway to any medical worker other than a worker who has switched the state of connection of the puncture needles (the arterial puncture needle (a) and the venous puncture needle (b)).

The blood purification apparatus further includes the index-changing unit that gives a change to the index of the blood extracorporeally circulating through the blood circuit 1. Furthermore, the detection of recirculating blood by the recirculating-blood-detecting unit (the first detecting unit E1 and the second detecting unit E2) and the calculation of recirculation rate (RR) by the recirculation-rate-calculating unit 11 are performed in accordance with the change given to the index of the blood from the index-changing unit. Therefore, the calculation of recirculation rate (RR) can be performed at any timing and with high accuracy.

The blood purification apparatus further includes the switching unit 13 for switching the mode from the treatment mode to the measurement mode. Therefore, the switching to the measurement mode can be performed easily and assuredly. Furthermore, the arterial closing unit Va and the venous closing unit Vb are openable and closable by the control unit 12. Furthermore, if the switching unit 13 is operated, the control unit 12 stops the blood pump 3 and causes the arterial closing unit Va and the venous closing unit Vb to close the distal portion of the arterial blood circuit 1a and the distal portion of the venous blood circuit 1b, respectively. Therefore, blood leakage from the distal portion of the arterial blood circuit 1a and the distal portion of the venous blood circuit 1b in the measurement mode can be prevented assuredly.

In addition, the control unit 12 controls the operation of the ultrafiltration pump 7. Furthermore, if the switching unit 13 is operated, the control unit 12 stops the blood pump 3 and the ultrafiltration pump 7. Therefore, in the measurement mode, the patient's blood can be assuredly prevented from being ultrafiltered. Furthermore, if the recirculation rate (RR) calculated in the treatment mode by the recirculation-rate-calculating unit 11 is higher than a predetermined value or if the venous pressure as the hydraulic pressure of the blood flowing in the venous blood circuit 1b in the treatment mode is higher than a predetermined value, it is enabled to provide corresponding information or to prevent the switching from the treatment mode to the measurement mode. Therefore, the safety of the patient at the switching to the measurement mode can be increased.

In particular, in the measurement mode, if reverse-connection confirmation that is enabled after the state of reverse connection is confirmed is performed, access-vessel blood flow rate (Qa) is calculated by causing the recirculating-blood-detecting unit (the first detecting unit E1 and the second detecting unit E2) to detect recirculating blood and the recirculation-rate-calculating unit 11 to calculate recirculation rate (RR). Furthermore, if normal-connection confirmation that is enabled after the state of normal connection is confirmed is performed, it is enabled to switch the mode from the measurement mode to the treatment mode. Therefore, the measurement of access-vessel blood flow rate (Qa) can be performed after the confirmation of the state of reverse connection, and the switching to the treatment mode can be performed after the confirmation of the state of normal connection.

Furthermore, in the treatment mode, the recirculating-blood-detecting unit (the first detecting unit E1 and the second detecting unit E2) is caused to detect recirculating blood, and the recirculation-rate-calculating unit 11 is caused to calculate recirculation rate (RR). Furthermore, if the mode once switched from the treatment mode to the measurement mode is reswitched to the treatment mode, it is enabled to compare the recirculation rate calculated in the earlier treatment mode and the recirculation rate calculated in the later treatment mode and to judge whether the state of normal connection is appropriate or not. Therefore, the judgement of the state of connection in the treatment mode can be made by using the recirculation rates (RR) calculated in the treatment mode.

In the treatment mode, venous pressure as the hydraulic pressure of blood flowing in the venous blood circuit 1b may be detected. Furthermore, if the mode once switched from the treatment mode to the measurement mode is reswitched to the treatment mode, the venous pressure detected in the earlier treatment mode and the venous pressure detected in the later treatment mode may be compared to judge whether the state of normal connection is appropriate or not. In such a case, the judgement of the state of connection in the treatment mode can be made by using the venous pressures detected in the treatment mode.

In addition, circulating-blood-volume rate of change (ΔBV) calculable from blood concentration that changes with ultrafiltration may be detected. Furthermore, after the mode is switched from the measurement mode to the treatment mode, whether the state of normal connection is appropriate or not may be judged in accordance with the change in the circulating-blood-volume rate of change (ΔBV). In such a case, the judgement of the state of connection in the treatment mode can be made by using the circulating-blood-volume rate of change (ΔBV) detected in the treatment mode.

While an embodiment has been described above, the present invention is not limited thereto. The state of reverse connection may be established as follows. While the arterial puncture needle (a) and the venous puncture needle (b) are kept in the puncturing state, the distal end of the arterial blood circuit 1a and the distal end of the venous blood circuit 1b are removed from the arterial puncture needle (a) and the venous puncture needle (b), respectively (see FIG. 10(a)). Subsequently, the venous puncture needle (b) is attached to the distal end of the arterial blood circuit 1a, and the arterial puncture needle (a) is attached to the distal end of the venous blood circuit 1b (see FIG. 10(b)). Thus, as illustrated in FIG. 9, the state where the downstream part of the access vessel is punctured with the puncture needle (the venous puncture needle (b)) at the distal end of the arterial blood circuit 1a and the upstream part of the access vessel is punctured with the puncture needle (the arterial puncture needle (a)) at the distal end of the venous blood circuit 1b is established.

Specifically, the arterial puncture needle (a) and the venous puncture needle (b) may each be a hemodialysis trocar catheter (a blood-vessel indwelling needle) including an indwelling-needle body illustrated in FIG. 10 and a metal inner needle (not illustrated). Such a hemodialysis trocar catheter includes, as illustrated in FIG. 10(a), the indwelling-needle body in which the arterial puncture needle (a) or the venous puncture needle (b) as a catheter, a distal part f made of rigid resin or the like, a clamping flexible tube g, and a joint c are integrated together; and the inner needle, which is not illustrated. The metal inner needle extends through the indwelling-needle body formed of the catheter (the arterial puncture needle (a) or the venous puncture needle (b)), the distal part f, the clamping flexible tube g, and the joint c. The patient is punctured with the inner needle and the catheter.

In a state where the patient is punctured with the inner needles and the catheters (the arterial puncture needle (a) and the venous puncture needle (b)), only the inner needles are removed from the patient. Thus, the indwelling-needle body including the arterial puncture needle (a) and the indwelling-needle body including the venous puncture needle (b) remain inside the patient's body. Therefore, when the distal end of the arterial blood circuit 1*a* and the distal end of the venous blood circuit 1*b* are connected to the joints c of the respective indwelling-needle bodies, the patient's blood can be made to extracorporeally circulate in the blood circuit through the arterial puncture needle (a) and the venous puncture needle (b).

More specifically, the arterial blood circuit 1*a* and the venous blood circuit 1*b* each have a joint d at the distal end thereof. The joint d is made of rigid resin or the like. As illustrated in FIG. 10(*b*), the joint c provided to the puncture needle is fitted onto the joint d and is fastened thereto with a lock ring R that is screwed thereon, whereby the fitted state can be locked. If the clamping flexible tube g is clamped with a clamp, a flow route between the arterial puncture needle (a) or the venous puncture needle (b) (the catheter) and the arterial blood circuit 1*a* or the venous blood circuit 1*b* can be blocked.

Hence, in the state of normal connection, when the lock rings R are loosened, the distal ends of the arterial blood circuit 1*a* and the venous blood circuit 1*b* can be removed from the arterial puncture needle (a) and the venous puncture needle (b) (the indwelling-needle bodies). Therefore, in a state where the arterial puncture needle (a) and the venous puncture needle (b) that are in normal connection are kept in the puncturing state, if the distal end of the arterial blood circuit 1*a* is connected to the venous puncture needle (b) and is locked with the lock ring R and the distal end of the venous blood circuit 1*b* is connected to the arterial puncture needle (a) and is locked with the lock ring R, the state of connection can be switched from normal connection to reverse connection.

That is, to switch the state of connection to reverse connection (the state illustrated in FIG. 9) from normal connection (the state illustrated in FIG. 2) where the upstream part of the access vessel is punctured with the puncture needle (the arterial puncture needle (a)) at the distal end of the arterial blood circuit 1*a* and the downstream part of the access vessel is punctured with the puncture needle (the venous puncture needle (b)) at the distal end of the venous blood circuit 1*b*, the lock rings R are loosened, and the distal end of the arterial blood circuit 1*a* and the distal end of the venous blood circuit 1*b* are removed from the respective indwelling-needle bodies while the patient is kept punctured with the arterial puncture needle (a) and the venous puncture needle (b) (the indwelling-needle bodies). Then, the distal end of the arterial blood circuit 1*a* is connected to the venous puncture needle (b), and the distal end of the venous blood circuit 1*b* is connected to the arterial puncture needle (a). Thus, as illustrated in FIG. 9, the state of reverse connection is established where the downstream part of the access vessel is punctured with the puncture needle (the venous puncture needle (b)) at the distal end of the arterial blood circuit 1*a* and the upstream part of the access vessel is punctured with the puncture needle (the arterial puncture needle (a)) at the distal end of the venous blood circuit 1*b*.

Likewise, to switch the state of connection to normal connection (the state illustrated in FIG. 2) from reverse connection (the state illustrated in FIG. 9) where the downstream part of the access vessel is punctured with the puncture needle (the venous puncture needle (b)) at the distal end of the arterial blood circuit 1*a* and the upstream part of the access vessel is punctured with the puncture needle (the arterial puncture needle (a)) at the distal end of the venous blood circuit 1*b*, the lock rings R are loosened, and the distal end of the arterial blood circuit 1*a* and the distal end of the venous blood circuit 1*b* are removed from the respective indwelling-needle bodies while the patient is kept punctured with the arterial puncture needle (a) and the venous puncture needle (b) (the indwelling-needle bodies). Then, the distal end of the arterial blood circuit 1*a* is connected to the arterial puncture needle (a), and the distal end of the venous blood circuit 1*b* is connected to the venous puncture needle (b). Thus, as illustrated in FIG. 2, the state of normal connection is established where the upstream part of the access vessel is punctured with the puncture needle (the arterial puncture needle (a)) at the distal end of the arterial blood circuit 1*a* and the downstream part of the access vessel is punctured with the puncture needle (the venous puncture needle (b)) at the distal end of the venous blood circuit 1*b*. In this case, the arterial puncture needle (a) and the venous puncture needle (b) are each a catheter. Alternatively, the arterial puncture needle (a) and the venous puncture needle (b) may each be a metal puncture needle as with the case of the above embodiment.

The index-changing unit may be any of the following, for example: a unit that instantly changes the composition of the dialysate flowing in the dialyzer 2 by changing, for a short time, the operating speed of a dialysate injection pump, not illustrated, connected to the dialysate introduction line L1 and thus causes a specific change; a unit that instantly raises or lowers the temperature of the dialysate flowing in the dialyzer 2 by raising or lowering, for a short time, the heating temperature of the heating unit H connected to the dialysate introduction line L1 and thus causes a specific change; a unit that allows manual injection of a diluent, such as a physiological saline solution, into a predetermined site of the blood circuit 1 (a position of the arterial blood circuit 1*a* that is nearer to the dialyzer 2 with respect to the first detecting unit E1) and thus instantly causes a specific change; and the like.

Moreover, the recirculating-blood-detecting unit (which may be a unit different from the first detecting unit E1 and the second detecting unit E2) may be caused to detect recirculating blood without changing the blood index by the index-changing unit. On the other hand, as long as the control unit 12 is capable of selectively executing the treatment mode and the measurement mode, the process of providing information and making confirmation in the measurement mode may be altered. That is, the entirety or part of the process of providing information and making confirmation may be omitted. While the above embodiments are each applied to a dialysis apparatus intended for dialysis treatment, the present invention may also be applied to any other blood purification apparatus (such as a blood purification apparatus or a plasma adsorption apparatus intended for hemodiafiltration, hemofiltration, or AFBF) that is capable of purifying blood of a patient while causing the blood to extracorporeally circulate.

The present invention is also applicable to any blood purification apparatus that has a different external shape, additional functions, and so forth, as long as the apparatus includes a control unit capable of executing a treatment mode in which blood purification treatment is performed with the blood purifier while the blood of the patient is caused to extracorporeally circulate through the blood circuit by activating the blood pump in a state of normal connection where an upstream part of the access vessel is punctured with the puncture needle at a distal end of the arterial blood circuit and a downstream part of the access vessel is punctured with the puncture needle at a distal end of the venous blood circuit; and a measurement mode in which the detection of recirculating blood by the recirculating-blood-detecting unit and the calculation of recirculation rate by the recirculation-rate-calculating unit are performed while the blood of the patient is caused to extracorporeally circulate through the blood circuit by activating the blood pump in a state of reverse connection where the downstream part of the access vessel is punctured with the puncture needle at the distal end of the arterial blood circuit and the upstream part of the access vessel is punctured with the puncture needle at the distal end of the venous blood circuit, the calculated recirculation rate being used in calculating blood flow rate in the access vessel that is calculable in the measurement mode.

REFERENCE SIGN LIST 1 blood circuit
1a arterial blood circuit
1b venous blood circuit
2 dialyzer (blood purifier)
3 blood pump
4 arterial air-trap chamber
5 venous air-trap chamber
6 duplex pump
7 ultrafiltration pump
8 pressurizing pump
9 degassing chamber
10 venous pressure sensor
11 recirculation-rate-calculating unit
12 control unit
13 switching unit
14 confirming unit
15 informing unit
16 judging unit
E1 first detecting unit (recirculating-blood-detecting unit)
E2 second detecting unit (recirculating-blood-detecting unit)
Va arterial closing unit
Vb venous closing unit

The invention claimed is:

1. A blood purification apparatus that includes
a blood circuit including an arterial blood circuit provided with an arterial puncture needle with which an access vessel of a patient is puncturable and a venous blood circuit provided with a venous puncture needle with which the access vessel is puncturable, the blood circuit allowing blood of the patient to extracorporeally circulate;
a blood purifier connected to the arterial blood circuit and to the venous blood circuit and that purifies the blood flowing through the blood circuit;
a blood pump provided to the arterial blood circuit;
a recirculating-blood-detecting unit capable of detecting recirculating blood when the blood of the patient is caused to extracorporeally circulate through the blood circuit by activating the blood pump, the recirculating blood being blood once returned to the patient from the venous blood circuit and reintroduced into the arterial blood circuit;
a recirculation-rate-calculating unit capable of calculating a recirculation rate, the recirculation rate being a proportion of the recirculating blood in the blood flowing in the arterial blood circuit,
wherein the blood purification apparatus comprising a control unit capable of executing:
a treatment mode in which blood purification treatment is performed with the blood purifier while the blood of the patient is caused to extracorporeally circulate through the blood circuit by activating the blood pump in a state of normal connection where an upstream part of the access vessel is punctured with the arterial puncture needle at a distal end of the arterial blood circuit and a downstream part of the access vessel is punctured with the venous puncture needle at a distal end of the venous blood circuit; and
a measurement mode in which the detection of recirculating blood by the recirculating-blood-detecting unit and the calculating of the recirculation rate by the recirculation-rate-calculating unit are performed while the blood of the patient is caused to extracorporeally circulate through the blood circuit by activating the blood pump in a state of reverse connection where the downstream part of the access vessel is punctured with the arterial puncture needle at the distal end of the arterial blood circuit and the upstream part of the access vessel is punctured with the venous puncture needle at the distal end of the venous blood circuit, the calculated recirculation rate being used in calculating blood flow rate in the access vessel that is calculable in the measurement mode,
a switching unit that switches a mode from the treatment mode to the measurement mode and
a confirming unit operable after a predetermined operation, the state of reverse connection, or the state of normal connection is confirmed,
wherein, in the treatment mode, the recirculating-blood-detecting unit is caused to detect recirculating blood and the recirculation-rate-calculating unit is caused to calculate recirculation rate; and wherein when the mode once switched from the treatment mode to the measurement mode is reswitched to the treatment mode, the control unit is enabled to compare a recirculation rate calculated in an earlier treatment mode and a recirculation rate calculated in a later treatment mode and to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit.

2. The blood purification apparatus according to claim 1, further comprising an index-changing unit that gives a change to an index of the blood extracorporeally circulating through the blood circuit, wherein the detection of recirculating blood by the recirculating-blood-detecting unit and the calculating of the recirculation rate by the recirculation-rate-calculating unit are performed in accordance with the change given to the index of the blood from the index-changing unit.

3. The blood purification apparatus according to claim 1, further comprising:
an arterial closing unit capable of closing a distal portion of the arterial blood circuit to block a flow route; and
a venous closing unit capable of closing a distal portion of the venous blood circuit to block a flow route,
wherein the arterial closing unit and the venous closing unit are openable and closable by the control unit, and
wherein when the switching unit is operated, the control unit stops the blood pump and causes the arterial closing unit and/or the venous closing unit to close the distal portion of the arterial blood circuit and/or the distal portion of the venous blood circuit, and wherein when the switching unit is operated, the blood pump and an ultrafiltration pump are stopped, and the arterial closing unit and the venous closing unit close the distal portion of the arterial blood circuit and the distal portion of the venous blood circuit.

4. The blood purification apparatus according to claim 3, further comprising an ultrafiltration pump for removing water from the blood flowing in the blood purifier, wherein the control unit controls an operation of the ultrafiltration pump, and wherein when the switching unit is operated, the control unit stops the blood pump and the ultrafiltration pump.

5. The blood purification apparatus according to claim 1, wherein when the recirculation rate calculated by the recirculation-rate-calculating unit in the treatment mode is higher than a predetermined value or when venous pressure as a hydraulic pressure of the blood flowing in the venous blood circuit in the treatment mode is higher than a predetermined value, the control unit is enabled to provide corresponding information or to prevent the switching from the treatment mode to the measurement mode.

6. The blood purification apparatus according to claim 1, wherein, in the measurement mode, when reverse-connection confirmation that is enabled after the state of reverse connection is confirmed is performed, the blood flow rate in the access vessel is calculated by causing the recirculating-blood-detecting unit to detect recirculating blood and the recirculation-rate-calculating unit to calculate recirculation rate; and wherein when normal-connection confirmation that is enabled after the state of normal connection is confirmed is performed, the control unit is enabled to switch the mode from the measurement mode to the treatment mode.

7. The blood purification apparatus according to claim 1, wherein, in the measurement mode, when the switching unit is operated, a voice prompts to confirm the state of reverse connection and to operate the confirming unit is outputted.

8. The blood purification apparatus according to claim 1, wherein when the switching unit is operated, the blood pump is stopped after closing the blood circuit with a closing unit so that operation of the measurement mode is initiated with the operation of the confirming unit.

9. A blood purification apparatus that includes
a blood circuit including an arterial blood circuit provided with an arterial puncture needle with which an access vessel of a patient is puncturable and a venous blood circuit provided with a venous puncture needle with which the access vessel is puncturable, the blood circuit allowing blood of the patient to extracorporeally circulate;
a blood purifier connected to the arterial blood circuit and to the venous blood circuit and that purifies the blood flowing through the blood circuit;
a blood pump provided to the arterial blood circuit;
a recirculating-blood-detecting unit capable of detecting recirculating blood when the blood of the patient is caused to extracorporeally circulate through the blood circuit by activating the blood pump, the recirculating blood being blood once returned to the patient from the venous blood circuit and reintroduced into the arterial blood circuit;
a recirculation-rate-calculating unit capable of calculating a recirculation rate, the recirculation rate being a proportion of the recirculating blood in the blood flowing in the arterial blood circuit,
wherein the blood purification apparatus comprising a control unit capable of executing:
a treatment mode in which blood purification treatment is performed with the blood purifier while the blood of the patient is caused to extracorporeally circulate through the blood circuit by activating the blood pump in a state of normal connection where an upstream part of the access vessel is punctured with the arterial puncture needle at a distal end of the arterial blood circuit and a downstream part of the access vessel is punctured with the venous puncture needle at a distal end of the venous blood circuit; and
a measurement mode in which the detection of recirculating blood by the recirculating-blood-detecting unit and the calculating of the recirculation rate by the recirculation-rate-calculating unit are performed while the blood of the patient is caused to extracorporeally circulate through the blood circuit by activating the blood pump in a state of reverse connection where the downstream part of the access vessel is punctured with the arterial puncture needle at the distal end of the arterial blood circuit and the upstream part of the access vessel is punctured with the venous puncture needle at the distal end of the venous blood circuit, the calculated recirculation rate being used in calculating blood flow rate in the access vessel that is calculable in the measurement mode,
a switching unit that switches a mode from the treatment mode to the measurement mode and
a confirming unit operable after a predetermined operation, the state of reverse connection, or the state of normal connection is confirmed;
wherein, in the treatment mode, venous pressure as a hydraulic pressure of the blood flowing in the venous blood circuit is detected; and wherein when the mode once switched from the treatment mode to the measurement mode is reswitched to the treatment mode, the control unit is enabled to compare a venous pressure detected in an earlier treatment mode and a venous pressure detected in a later treatment mode and to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit.

10. The blood purification apparatus according to claim 9, wherein when the recirculation rate calculated by the recirculation-rate-calculating unit in the treatment mode is higher than a predetermined value or when venous pressure as a hydraulic pressure of the blood flowing in the venous blood circuit in the treatment mode is higher than a predetermined value, the control unit is enabled to provide corresponding information or to prevent the switching from the treatment mode to the measurement mode.

11. The blood purification apparatus according to claim 9, wherein, in the measurement mode, when reverse-connection confirmation that is enabled after the state of reverse connection is confirmed is performed, the blood flow rate in the access vessel is calculated by causing the recirculating-blood-detecting unit to detect recirculating blood and the recirculation-rate-calculating unit to calculate recirculation rate; and wherein when normal-connection confirmation that is enabled after the state of normal connection is confirmed is performed, the control unit is enabled to switch the mode from the measurement mode to the treatment mode.

12. The blood purification apparatus according to claim 9, wherein, in the treatment mode, the recirculating-blooddetecting unit is caused to detect recirculating blood and the recirculation-rate-calculating unit is caused to calculate recirculation rate; and wherein when the mode once switched from the treatment mode to the measurement mode is reswitched to the treatment mode, the control unit is enabled to compare a recirculation rate calculated in an earlier treatment mode and a recirculation rate calculated in a later treatment mode and to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit.

13. The blood purification apparatus according to claim 9, wherein, in the treatment mode, venous pressure as a hydraulic pressure of the blood flowing in the venous blood circuit is detected; and wherein when the mode once switched from the treatment mode to the measurement mode is reswitched to the treatment mode, the control unit is enabled to compare a venous pressure detected in an earlier treatment mode and a venous pressure detected in a later treatment mode and to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit.

14. The blood purification apparatus according to claim 9, wherein, in the treatment mode, circulating-blood-volume rate of change calculable from blood concentration that changes with ultrafiltration is detected; and wherein after the mode is switched from the measurement mode to the treatment mode, the control unit is enabled to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit in accordance with a change in the circulating-blood-volume rate of change.

15. The blood purification apparatus according to claim 9, wherein with the control unit, in the treatment mode, when the confirming unit is operated after the state of reverse connection is confirmed, the blood flow rate in the access vessel is calculated by causing the recirculating-blood-detecting unit to detect recirculating blood and the recirculation-rate-calculating unit to calculate recirculation rate; and wherein when the confirming unit is operated after the state of normal connection is confirmed, the control unit is enabled to switch the mode from the measurement mode to the treatment mode.

16. A blood purification apparatus that includes
a blood circuit including an arterial blood circuit provided with an arterial puncture needle with which an access vessel of a patient is puncturable and a venous blood circuit provided with a venous puncture needle with which the access vessel is puncturable, the blood circuit allowing blood of the patient to extracorporeally circulate;
a blood purifier connected to the arterial blood circuit and to the venous blood circuit and that purifies the blood flowing through the blood circuit;
a blood pump provided to the arterial blood circuit;
a recirculating-blood-detecting unit capable of detecting recirculating blood when the blood of the patient is caused to extracorporeally circulate through the blood circuit by activating the blood pump, the recirculating blood being blood once returned to the patient from the venous blood circuit and reintroduced into the arterial blood circuit;
a recirculation-rate-calculating unit capable of calculating a recirculation rate, the recirculation rate being a proportion of the recirculating blood in the blood flowing in the arterial blood circuit,
wherein the blood purification apparatus comprising a control unit capable of executing:
a treatment mode in which blood purification treatment is performed with the blood purifier while the blood of the patient is caused to extracorporeally circulate through the blood circuit by activating the blood pump in a state of normal connection where an upstream part of the access vessel is punctured with the arterial puncture needle at a distal end of the arterial blood circuit and a downstream part of the access vessel is punctured with the venous puncture needle at a distal end of the venous blood circuit; and
a measurement mode in which the detection of recirculating blood by the recirculating-blood-detecting unit and the calculating of the recirculation rate by the recirculation-rate-calculating unit are performed while the blood of the patient is caused to extracorporeally circulate through the blood circuit by activating the blood pump in a state of reverse connection where the downstream part of the access vessel is punctured with the arterial puncture needle at the distal end of the arterial blood circuit and the upstream part of the access vessel is punctured with the venous puncture needle at the distal end of the venous blood circuit, the calculated recirculation rate being used in calculating blood flow rate in the access vessel that is calculable in the measurement mode,
a switching unit that switches a mode from the treatment mode to the measurement mode and
a confirming unit operable after a predetermined operation, the state of reverse connection, or the state of normal connection is confirmed;
wherein, in the treatment mode, circulating-blood-volume rate of change calculable from blood concentration that changes with ultrafiltration is detected; and wherein after the mode is switched from the measurement mode to the treatment mode, the control unit is enabled to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit in accordance with a change in the circulating-blood-volume rate of change.

17. The blood purification apparatus according to claim 16, wherein, in the treatment mode, the recirculating-blood-detecting unit is caused to detect recirculating blood and the recirculation-rate-calculating unit is caused to calculate recirculation rate; and wherein when the mode once switched from the treatment mode to the measurement mode is reswitched to the treatment mode, the control unit is enabled to compare a recirculation rate calculated in an earlier treatment mode and a recirculation rate calculated in a later treatment mode and to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit.

18. The blood purification apparatus according to claim 16, further comprising an index-changing unit that gives a change to an index of the blood extracorporeally circulating through the blood circuit, wherein the detection of recirculating blood by the recirculating-blood-detecting unit and the calculating of the recirculation rate by the recirculation-rate-calculating unit are performed in accordance with the change given to the index of the blood from the index-changing unit.

19. The blood purification apparatus according to claim 16, further comprising:
- an arterial closing unit capable of closing a distal portion of the arterial blood circuit to block a flow route; and a venous closing unit capable of closing a distal portion of the venous blood circuit to block a flow route, wherein the arterial closing unit and the venous closing unit are openable and closable by the control unit, and wherein when the switching unit is operated, the control unit stops the blood pump and causes the arterial closing unit and/or the venous closing unit to close the distal portion of the arterial blood circuit and/or the distal portion of the venous blood circuit, and
- an ultrafiltration pump for removing water from the blood flowing in the blood purifier, wherein the control unit controls an operation of the ultrafiltration pump, and wherein when the switching unit is operated, the control unit stops the blood pump and the ultrafiltration pump, wherein when the switching unit is operated, the blood pump and an ultrafiltration pump are stopped, and the arterial closing unit and the venous closing unit close the distal portion of the arterial blood circuit and the distal portion of the venous blood circuit.

20. The blood purification apparatus according to claim 16, wherein when the recirculation rate calculated by the recirculation-rate-calculating unit in the treatment mode is higher than a predetermined value or when venous pressure as a hydraulic pressure of the blood flowing in the venous blood circuit in the treatment mode is higher than a predetermined value, the control unit is enabled to provide corresponding information or to prevent the switching from the treatment mode to the measurement mode;

wherein, in the measurement mode, when reverse-connection confirmation that is enabled after the state of reverse connection is confirmed is performed, the blood flow rate in the access vessel is calculated by causing the recirculating-blood-detecting unit to detect recirculating blood and the recirculation-rate-calculating unit to calculate recirculation rate;

wherein when normal-connection confirmation that is enabled after the state of normal connection is confirmed is performed, the control unit is enabled to switch the mode from the measurement mode to the treatment mode; and wherein, in the treatment mode, the recirculating-blood-detecting unit is caused to detect recirculating blood and the recirculation-rate-calculating unit is caused to calculate recirculation rate; and wherein when the mode once switched from the treatment mode to the measurement mode is reswitched to the treatment mode, the control unit is enabled to compare a recirculation rate calculated in an earlier treatment mode and a recirculation rate calculated in a later treatment mode and to judge whether the state of normal connection is created where an upstream part of the access vessel is punctured with the arterial puncture needle at a distal end of the arterial blood circuit and a downstream part of the access vessel is punctured with the venous puncture needle at a distal end of the venous blood circuit.

* * * * *